United States Patent
Bono-Combie et al.

(10) Patent No.: US 7,320,982 B2
(45) Date of Patent: Jan. 22, 2008

(54) USE OF 4-SUBSTITUTED TETRAHYDROPYRIDINES FOR THE MANUFACTURE OF MEDICAMENTS ACTING UPON TGF-β 1

(75) Inventors: Françoise Bono-Combie, Toulouse (FR); Jacqueline Fournier, Plaisance du Touch (FR); Jean Marc Herbert, Tournefeuille (FR); Isabelle Lamarche, Lara (FR); Umberto Guzzi, Milan (IT)

(73) Assignee: sanofi-aventis, Paris (FR)

( * ) Notice: Subject to any disclaimer, the term of this patent is extended or adjusted under 35 U.S.C. 154(b) by 151 days.

(21) Appl. No.: 10/773,073

(22) Filed: Feb. 5, 2004

(65) Prior Publication Data

US 2004/0157868 A1 Aug. 12, 2004

Related U.S. Application Data

(62) Division of application No. 10/044,223, filed on Nov. 20, 2001, now Pat. No. 6,693,118, which is a division of application No. 09/423,884, filed as application No. PCT/FR98/01000 on May 20, 1998, now Pat. No. 6,342,505.

(30) Foreign Application Priority Data

May 28, 1997 (FR) .................... 97 06522

(51) Int. Cl.
*A61K 31/443* (2006.01)
*A61K 31/44* (2006.01)
(52) U.S. Cl. ..................................... 514/277
(58) Field of Classification Search ............... 514/299, 514/317, 277
See application file for complete search history.

(56) References Cited

U.S. PATENT DOCUMENTS

| | | | |
|---|---|---|---|
| 4,521,428 | A | 6/1985 | Nisato et al. |
| 5,229,389 | A | 7/1993 | Coude et al. |
| 5,270,320 | A | 12/1993 | Coude et al. |
| 5,281,606 | A | 1/1994 | Guzzi et al. |
| 5,292,745 | A | 3/1994 | Heaulme et al. |
| 5,462,945 | A | 10/1995 | Guzzi et al. |
| 5,468,753 | A | 11/1995 | Coude et al. |
| 5,618,822 | A | 4/1997 | Guzzi et al. |
| 5,981,754 | A | 11/1999 | Badoni et al. |
| 6,034,090 | A | 3/2000 | Baroni et al. |
| 6,342,505 | B1 * | 1/2002 | Bono-Combie et al. .... 514/277 |

FOREIGN PATENT DOCUMENTS

| | | |
|---|---|---|
| EP | 101381 | 2/1984 |
| EP | 0458696 | 11/1991 |
| EP | 0458697 | 11/1991 |
| EP | 0498718 | 8/1992 |
| EP | 0645755 | 3/1995 |
| WO | WO 93/11107 | 6/1993 |
| WO | WO 96/21449 | 7/1996 |
| WO | WO 97/01536 | 1/1997 |

OTHER PUBLICATIONS

Tashiro et al., Differential Expression of Transforming Growth Factor-β Isoforms in Human Prion Diseases, Neuropath. Appl. Neuro., 24:284-292 (1998).*
The Center for Healthy Aging's Helpguide online at http://www.helpguide.org/elder/creutzfeldt_jakob.htm.*
J. H. Prehn, Medline Abstract No. 96226070.
J. P. Terranova, Medline Abstract No. 97011603.
J. Mathieu, Medline Abstract No. 97112057.
Derwent Patent Abstract No. 199709.
Boche et al., TGFBeta1 regulates the inflammatory response during chronic neurodegeneration, Neurobiology of Disease, vol. 22, 2006, pp. 638-650.
Cunningham et al., Transforming growth factor Beta1, the dominant cytokine in murine prion disease: influence on inflammatory cytokine synthesis and alteration of vascular extracellular matrix, Neuropathology and Applied Neurobiology, vol. 28, 2002, pp. 107-119.
Kempster et al., Time of transforming growth factor beta 1 inoculation alters the incubation of BSE in mice, Neuroreport, vol. 15, No. 14, Oct. 2004, pp. 2233-2236.

\* cited by examiner

*Primary Examiner*—Patricia L. Morris
(74) *Attorney, Agent, or Firm*—Karen I. Krupen

(57) ABSTRACT

The invention relates to the use of a compound of formula (I):

$$R_1 - \text{(Ar)} - Y - \text{(tetrahydropyridine)} - N - CH_2 - \underset{Z''\ Z'}{C} - Z \quad (I)$$

for the preparation of pharmaceutical compositions for increasing the circulating, cellular and extracellular levels of TGF-β1.

1 Claim, No Drawings

USE OF 4-SUBSTITUTED TETRAHYDROPYRIDINES FOR THE MANUFACTURE OF MEDICAMENTS ACTING UPON TGF-β 1

This application is a divisional of U.S. Application Ser. No. 10/044,223 filed Nov. 20, 2001 now U.S. Pat. No. 6,693,118, which in turn is a divisional of U.S. Application Ser. No. 09/423,884 filed Apr. 10, 2000, now U.S. Pat. No. 6,342,505, which in turn is a 35 U.S.C. § 371 application of PCT International Application No. PCT/FR98/01000 filed May 20, 1998.

The present invention relates to the use of certain 1,2,3,6-tetrahydropyridine derivatives, and to their pharmaceutically acceptable salts and solvates for the preparation of medicaments capable of increasing the levels of TGF-β1 (Transforming growth factor-β1).

TGF-β1 is a multifunctional and ubiquitous peptide which is constituted, in its active form, by two identical sub-units linked by a disulphide bridge. As illustrated by P. Bedesse and V. Paradis (Journal of Hepatology, 1995, 22, 37-42), TGF-β1 has been identified as a factor which induces cell growth in transformed fibroblasts, but many other cell functions have been discovered successively.

The WO 93/09808 application describes the use of TGF-β1 for the treatment of damages to the central nervous system.

The WO 96/34881 and WO 94/17099 applications claim novel peptides which have a similar activity to that of TGF-β1 and which may be used for the treatment of several pathologies.

TGF-β1 is for example implicated in the control of the cell cycle, in angiogenesis, in cellular differentiation, in embryogenesis, in tissue repair, as well as in apoptosis.

Amongst these activities, the anti-apoptotic effect of TGF-β1 is very important due to its pharmacological implications.

"Apoptosis", or "programmed cell death", indicates the whole of the physiological processes linked to cell death. In its terminal phase, apoptosis is characterised by an activation of the endonucleases which cleave double-stranded DNA in the internucleosomal regions, thus generating mono- and oligo-nucleosomes which complex with histones. An enrichment in oligo- and mono-nucleosomes linked to histones is thus observed in the cytoplasm of the apoptotic cells.

Although this phenomenon is physiological, in contrast to necrosis, it may also be caused by pathological stimulations.

D. A. Carson and J. M. Ribeiro report (The Lancet 1993, 341, 1251-1254) the role of apoptosis in certain pathologies such as immuno-depression, immune deficiencies in patients suffering from AIDS, cell aging, and degenerative illnesses.

J. Mathieu et al. (Ann. pharmaceutiques francaises 1996, 54, 5, 193-201) demonstrated that the pathological effects caused by chemical and physical agents such as free radicals and ionising radiation are caused by the pro-apoptotic effects of these agents.

The apoptosis-regulating products were described in the WO 96/21449 patent application. The general formula includes both inhibitors and stimulators of apoptosis, without the means of distinguishing them from one another being given.

It has now been found that certain tetrahydropyridines increase circulating and cellular and extracellular levels of TGF-β1.

Thus, the object of the present invention is the use of a 4-substituted 1,2,3,6-tetrahydropyridine of formula (I):

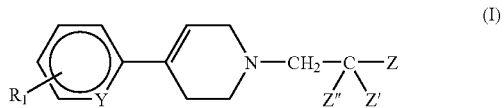

in which:
R$_1$ represents a halogen or a CF$_3$, (C$_1$-C$_4$)alkyl or (C$_1$-C$_4$)alkoxy group;
Y represents a nitrogen atom or a CH group;
Z' and Z" each represent hydrogen or a (C$_1$-C$_3$)alkyl group, or one represents hydrogen and the other a hydroxy group, or both, together, represent an oxo group;
Z represents
 a phenyl radical;
 a phenyl radical monosubstituted with a substituent X, X being
  a) a (C$_1$-C$_6$)alkyl; (C$_1$-C$_6$)alkoxy; (C$_3$-C$_7$)carboxyalkyl; (C$_1$-C$_4$)alkoxycarbonyl(C$_1$-C$_6$)alkyl; (C$_3$-C$_7$)carboxyalkoxy or (C$_1$-C$_4$)-alkoxycarbonyl(C$_1$-C$_6$)alkoxy group;
  b) a group selected from a (C$_3$-C$_7$)cycloalkyl, (C$_3$-C$_7$)cycloalkyloxy, (C$_3$-C$_7$)cycloalkylmethyl, (C$_3$-C$_7$)cycloalkylamino and cyclohexenyl group, it being possible for said group to be substituted with a halogen, hydroxy, (C$_1$-C$_4$)alkoxy, carboxy, (C$_1$-C$_4$)alkoxycarbonyl, amino, mono- or di-(C$_1$-C$_4$)alkylamino;
  c) a group selected from a phenyl, phenoxy, phenylamino, N—(C$_1$-C$_3$)alkylphenylamino, phenylmethyl, phenylethyl, phenylcarbonyl, phenylthio, phenylsulphonyl, phenylsulphinyl or styryl, it being possible for said group to be mono- or poly-substituted on the phenyl group with a halogen, CF$_3$, (C$_1$-C$_4$)alkyl, (C$_1$-C$_4$)alkoxy, cyano, amino, mono- or di-(C$_1$-C$_4$)alkylamino, (C$_1$-C$_4$) acylamino, carboxy, (C$_1$-C$_4$)alkoxycarbonyl, aminocarbonyl, mono- or di-(C$_1$-C$_4$)alkylaminocarbonyl, amino(C$_1$-C$_4$)alkyl, hydroxy(C$_1$-C$_4$)alkyl or halo(C$_1$-C$_4$)alkyl;
 a phenyl radical disubstituted with a substituent R$_2$, R$_2$ being a halogen or a hydroxy, methyl, ethyl, (C$_3$-C$_6$) alkyl, (C$_1$-C$_4$)alkoxy or trifluoromethyl group and with a substituent X, X being as defined above;
 a 1-naphthyl or 2-naphthyl radical;
 a 1-naphthyl or 2-naphthyl radical substituted in positions 5, 6, 7 and/or 8 with one or two hydroxyl groups, one or two (C$_1$-C$_4$)alkoxy groups or a 6,7-methylenedioxy group;
or Z" is hydrogen and Z and Z' represent, each independently, a non-substituted or mono-, di- or tri-substituted phenyl group;
or of one of its pharmaceutically acceptable salts and solvates, for the preparation of pharmaceutical compositions capable of increasing circulating and cellular and extracellular levels of TGF-β$_1$.

According to an advantageous aspect, the object of the invention is the use of the compound of formula (I) in which Y is CH and R$_1$ is o- or m-CF$_3$.

According to a preferred aspect, Y is CH, R$_1$ is o- or m-CF$_3$ and Z' and Z" are hydrogen.

According to another preferred aspect, Y is CH, R$_1$ is o- or m-CF$_3$, Z' and Z" represent an oxo group and Z is 4-biphenyl.

According to a further advantageous aspect, the object of the invention is the use of the compound of formula (I) wherein Y is CH, $R_1$ is o- or m-$CF_3$, Z' and Z" are hydrogen and Z represents a phenyl radical monosubstituted with a substituent X, X being a), b), c) or one of its pharmaceutically acceptable salts and solvates.

According to another preferred aspect, the invention relates to the use of the compound of formula (I) in which Y is CH, $R_1$ is o- or m-$CF_3$, Z' and Z" are hydrogen and Z represents either a phenyl radical monosubstituted with a group X', X' being a phenyl non-substituted or substituted with 1 to 3 halogens, 1 to 3 $CF_3$, 1 to 3 ($C_1$-$C_4$)alkyl, 1 to 3 ($C_1$-$C_4$)alkoxy, 1 to 3 cyano, 1 to 3 amino, 1 to 3 mono- or di-($C_1$-$C_4$)alkylamino, 1 to 3 ($C_1$-$C_4$)acylamino, 1 to 3 carboxy, 1 to 3 ($C_1$-$C_4$)alkoxycarbonyl, 1 to 3 aminocarbonyl, 1 to 3 mono- or di-($C_1$-$C_4$)alkylaminocarbonyl, 1 to 3 amino($C_1$-$C_4$)alkyl, 1 to 3 hydroxy($C_1$-$C_4$)alkyl or 1 to 3 halo($C_1$-$C_4$)alkyl groups; or a phenyl radical disubstituted with a substituent $R_2$, $R_2$ being a halogen or a hydroxy, methyl, ethyl, ($C_3$-$C_6$)alkyl, ($C_1$-$C_4$)alkoxy or trifluoromethyl group and with a substituent X', X' being as defined above, or of one of its pharmaceutically acceptable salts and solvates.

According to another preferred aspect, the invention relates to the use of the compound of formula (I) in which Y is CH, $R_1$ is o- or m-$CF_3$, Z' and Z" are hydrogen and Z is a phenyl group substituted in positions 3 and 4 with a ($C_1$-$C_6$)alkyl group, or of one of its pharmaceutically acceptable salts and solvates.

According to another preferred aspect, the invention relates to the use of the compound of formula (I) in which Y is CH, $R_1$ is o- or m-$CF_3$, Z" is hydrogen and Z and Z', identical, each represent a phenyl group; a phenyl group substituted in position 2, 3 or 4 with a fluorine or chlorine atom or with a methyl, ethyl, n-propyl, i-propyl n-butyl, i-butyl, s-butyl, t-butyl, trifluoromethyl, cyano, methoxy, methylthio, methylsulphonyl, ethoxy, ethylthio, ethylsulphonyl, ($C_1$-$C_3$)alkoxycarbonyl or di($C_1$-$C_3$)alkylaminocarbonyl group; a phenyl group disubstituted in positions 2,4; 3,4; 3,5 or 2,6 with a chlorine or fluorine atom, or with a methyl, ethyl, trifluoromethyl, cyano or methoxy group; or a phenyl group trisubstituted in positions 3,4,5; 2,4,5 or 2,4,6 with a chlorine or fluorine atom, or with a methyl, ethyl, trifluoromethyl, cyano or methoxy group, or of one of its pharmaceutically acceptable salts and solvates.

According to a particularly preferred aspect, the invention relates to the use of the compound of formula (I) in which Y is CH, $R_1$ is m-trifluoromethyl, Z' and Z" are hydrogen and Z represents a naphthyl, 6,7-dimethoxy-2-naphthyl or 6,7-methylenedioxy-2-naphthyl group, or of one of its pharmaceutically acceptable salts and solvates.

A particularly advantageous compound according to the present invention may be selected amongst:

1-(2-naphth-2-ylethyl)-4-(3-trifluoromethylphenyl)-1,2,3,6-tetrahydropyridine;
1-[2-(6,7-dimethoxynaphth-2-yl)ethyl]-4-(3-trifluoromethylphenyl)-1,2,3,6-tetrahydropyridine;
1-[2-(6,7-methylenedioxynaphth-2-yl)ethyl]-4-(3-trifluoromethylphenyl)-1,2,3,6-tetrahydropyridin
1-[2-(4-isobutylphenyl)propyl]-4-(3-trifluoromethylphenyl)-1,2,3,6-tetrahydropyridine;
1-[(2S)-2-(4-isobutylphenyl)propyl]-4-(3-trifluoromethylphenyl)-1,2,3,6-tetrahydropyridine;
1-[(2R)-2-(4-isobutylphenyl)propyl]-4-(3-trifluoromethylphenyl)-1,2,3,6-tetrahydropyridine;
1-[2-(4-isobutylphenyl)ethyl]-4-(3-trifluoromethylphenyl)-1,2,3,6-tetrahydropyridine;
1-[2-(4-tertbutylphenyl)ethyl]-4-(3-trifluoromethylphenyl)-1,2,3,6-tetrahydropyridine;
1-[2-(4-isobutylphenyl)-2-methylpropyl]-4-(3-trifluoromethylphenyl)-1,2,3,6-tetrahydropyridine
1-[2-(4-isopropylphenyl)ethyl]-4-(3-trifluoromethylphenyl)-1,2,3,6-tetrahydropyridine;
1-[2-(3'-chloro-4-biphenylyl)ethyl]-4-(3-trifluoromethylphenyl)-1,2,3,6-tetrahydropyridine;
1-[2-(2'-chloro-4-biphenylyl)ethyl]-4-(3-trifluoromethylphenyl)-1,2,3,6-tetrahydropyridine;
1-[2-(4'-chloro-4-biphenylyl)ethyl]-4-(3-trifluoromethylphenyl)-1,2,3,6-tetrahydropyridine;
1-[2-(4'-fluoro-4-biphenylyl)ethyl]-4-(3-trifluoromethylphenyl)-1,2,3,6-tetrahydropyridine;
1-[2-(3'-trifluoromethyl-4-biphenylyl)ethyl]-4-(3-trifluoromethylphenyl)-1,2,3,6-tetrahydropyridine;
1-[2-(4-cyclohexylphenyl)ethyl]-4-(3-trifluoromethylphenyl)-1,2,3,6-tetrahydropyridine;
1-[2-(4-biphenylyl)-2-ethyl]-4-(4-fluorophenyl)-1,2,3,6-tetrahydropyridine;
1-[2-(4-biphenylyl)-2-methylpropyl]-4-(3-trifluoromethylphenyl)-1,2,3,6-tetrahydropyridine;
1-[2-(4-phenoxyphenyl)-2-ethyl]-4-(3-trifluoromethylphenyl)-1,2,3,6-tetrahydropyridine;
1-[2-(4-benzylphenyl)-2-ethyl]-4-(3-trifluoromethylphenyl)-1,2,3,6-tetrahydropyridine;
1-[2-(4-n-butylphenyl)ethyl]-4-(3-trifluoromethylphenyl)-1,2,3,6-tetrahydropyridine;
1-[2-(4-biphenylyl)ethyl]-4-(3-trifluoromethylphenyl)-1,2,3,6-tetrahydropyridine;
1-[2-(4-n-butoxyphenyl)ethyl]-4-(3-trifluoromethylphenyl)-1,2,3,6-tetrahydropyridine;
1-[2-(3,4-diethylphenyl)ethyl]-4-(3-trifluoromethylphenyl)-1,2,3,6-tetra-hydropyridine;
1-[2-(3-methyl-4-pentylphenyl)ethyl]-4-(3-trifluoromethylphenyl)-1,2,3,6-tetrahydropyridine;
1-[2-(4-methyl-3-pentylphenyl)ethyl]-4-(3-trifluoromethylphenyl)-1,2,3,6-tetrahydropyridine;
1-[2-(3,4-diethylphenyl)ethyl]-4-(6-chloropyrid-2-yl)-1,2,3,6-tetrahydropyridine;
1-(2,2-diphenylethyl)-4-(3-trifluoromethylphenyl)-1,2,3,6-tetrahydropyridine;
1-[2,2-(4,4'-dichlorodiphenyl)ethyl]-4-(3-trifluoromethylphenyl)-1,2,3,6-tetrahydropyridine;
1-[2,2-(3,3'-bistrifluoromethyldiphenyl)ethyl]-4-(3-trifluoromethylphenyl)-1,2,3,6-tetrahydropyridine;
1-[2,2-(4,4'-dimethoxydiphenyl)ethyl]-4-(3-trifluoromethylphenyl)-1,2,3,6-tetrahydropyridine;
1-[2-(4-fluorophenyl)-2-phenylethyl]-4-(3-trifluoromethylphenyl)-1,2,3,6-tetrahydropyridine;
1-(3,3-diphenylpropyl)-4-(3-trifluoromethylphenyl)-1,2,3,6-tetrahydropyridine;
1-[2,2-(4,4'-dichlorodiphenyl)ethyl]-4-(6-chloropyrid-2-yl)-1,2,3,6-tetrahydropyridine;
1-[2-(3'-chlorobiphenyl-4-yl)-2-oxoethyl]-4-(3-trifluoromethylphenyl)-1,2,3,6-tetrahydropyridine;
1-[2-(2'-chlorobiphenyl-4-yl)-2-oxoethyl]-4-(3-trifluoromethylphenyl)-1,2,3,6-tetrahydropyridine;
1-[2-(4'-chlorobiphenyl-4-yl)-2-oxoethyl]-4-(3-trifluoromethylphenyl)-1,2,3,6-tetrahydropyridine;
1-[2-(4-isobutylphenyl)-2-oxoethyl]-4-(3-trifluoromethylphenyl)-1,2,3,6-tetrahydropyridine;
1-[2-(4-benzylphenyl)-2-oxoethyl]-4-(3-trifluoromethylphenyl)-1,2,3,6-tetrahydropyridine;
1-[2-(4-cyclohexylphenyl)-2-oxoethyl]-4-(3-trifluoromethylphenyl)-1,2,3,6-tetrahydropyridine;

1-[2-(4'-fluorobiphenyl-4-yl)-2-oxoethyl]-4-(3-trifluoromethylphenyl)-1,2,3,6-tetrahydropyridine;
1-[2-(4-n-butylphenyl)-2-oxoethyl]-4-(3-trifluoromethylphenyl)-1,2,3,6-tetrahydropyridine;
1-[2-(biphenyl-4-yl)-2-oxoethyl]-4-(3-trifluoromethylphenyl)-1,2,3,6-tetrahydropyridine;
1-[2-(4-t-butylphenyl)-2-oxoethyl]-4-(3-trifluoromethylphenyl)-1,2,3,6-tetrahydropyridine;
1-[2-(4'-trifluoromethylbiphenyl-4-yl)-2-oxoethyl]-4-(3-trifluoromethylphenyl)-1,2,3,6-tetrahydropyridine;
1-[2-(2,3'-dichloro-4-biphenylyl)ethyl]-4-(3-trifluoromethylphenyl)-1,2,3,6-tetrahydropyridine;
1-[2-(3-chloro-4-biphenylyl)ethyl]-4-(3-trifluoromethylphenyl)-1,2,3,6-tetrahydropyridine;
1-[2-(3',5'-dichloro-4-biphenylyl)ethyl]-4-(3-trifluoromethylphenyl)-1,2,3,6-tetrahydropyridine;
1-[2-(2',4'-dichloro-4-biphenylyl)ethyl]-4-(3-trifluoromethylphenyl)-1,2,3,6-tetrahydropyridine;
1-[2-(2-chloro-4-biphenylyl)ethyl]-4-(3-trifluoromethylphenyl)-1,2,3,6-tetrahydropyridine;
1-[2-(3'-chloro-4-biphenylyl)-2-methylpropyl]-4-(3-trifluoromethylphenyl)-1,2,3,6-tetrahydropyridine;
1-[2-(2-fluoro-4-biphenylyl)propyl]-4-(3-trifluoromethylphenyl)-1,2,3,6-tetrahydropyridine;
1-[2-(4-methoxy-3-biphenylyl)ethyl]-4-(3-trifluoromethylphenyl)-1,2,3,6-tetrahydropyridine;
1-[2-(4'-methoxy-4-biphenylyl)ethyl]-4-(3-trifluoromethylphenyl)-1,2,3,6-tetrahydropyridine
1-[2-(4'-hydroxy-4-biphenylyl)ethyl]-4-(3-trifluoromethylphenyl)-1,2,3,6-tetrahydropyridine
1-[2-(4'-ethoxycarbonylbutoxy-4-biphenylyl)ethyl]-4-(3-trifluoromethylphenyl)-1,2,3,6-tetrahydropyridine;
1-[2-(3-biphenylyl)ethyl]-4-(3-trifluoromethylphenyl)-1,2,3,6-tetrahydropyridine;
1-[2-(3'chloro-4'-fluoro-4-biphenylyl)ethyl]-4-(3-trifluoromethylphenyl)-1,2,3,6-tetrahydropyridine;
1-[2-(2'-trifluoromethyl-4-biphenylyl)ethyl]-4-(3-trifluoromethylphenyl)-1,2,3,6-tetrahydropyridine;
1-[2-(biphenyl-4-yl)ethyl]-4-(2-trifluoromethylphenyl)-1,2,3,6-tetrahydropyridine;
1-[2-(4-cyclohexenylphenyl)ethyl]-4-(3-trifluoromethylphenyl)-1,2,3,6-tetrahydropyridine;
1-[2-(3,4-diisobutylphenyl)ethyl]-4-(3-trifluoromethylphenyl)-1,2,3,6-tetrahydropyridine;
1-[2-(3,4-dipropylphenyl)ethyl]-4-(3-trifluoromethylphenyl)-1,2,3,6-tetrahydropyridine;
1-[2-(4-cyclohexylphenyl)ethyl]-4-(6-chloropyrid-2-yl)-1,2,3,6-tetrahydropyridine;
1-[2-(4-isobutylphenyl)propyl]-4-(6-chloropyrid-2-yl)-1,2,3,6-tetrahydropyridine;
1-[2-(2'-trifluoromethylbiphenyl-4-yl)-2-oxoethyl]-4-(3-trifluoromethylphenyl)-1,2,3,6-tetrahydropyridine;
1-[2-(3'-trifluoromethylbiphenyl-4-yl)-2-oxoethyl]-4-(3-trifluoromethylphenyl)-1,2,3,6-tetrahydropyridine;
and their pharmaceutically acceptable salts and solvates.

1-(2-naphth-2-ylethyl)-4-(3-trifluoromethylphenyl)-1,2,3,6-tetrahydropyridine, known by its laboratory code SR 57746 and its pharmaceutically acceptable salts and solvates, especially its hydrochloride (SR 57746A), are particularly preferred compounds for the use according to the present invention.

Certain compounds of formula (I) are novel products. Thus, according to another of its aspects, the present invention relates to a compound of formula (I) selected amongst:
1-[2-(6,7-methylenedioxynaphth-2-yl)ethyl]-4-(3-trifluoromethylphenyl)-1,2,3,6-tetrahydropyridine,
1-[2-(4-cyclohexenylphenyl)ethyl]-4-(3-trifluoromethylphenyl)-1,2,3,6-tetrahydropyridine, and
1-[2-(biphenyl-4-yl)ethyl]-4-(2-trifluoromethylphenyl)-1,2,3,6-tetrahydropyridine, and their pharmaceutically acceptable salts and solvates.

The salts with pharmaceutically acceptable bases are for example those with alkali metals or alkaline earth metals, such as sodium, potassium, calcium, magnesium, and those with organic bases, such as amines, basic amino acids (lysine, arginine, histidine), trometamol, N-methylglutamine, etc.

The salts with pharmaceutically acceptable acids are for example those with mineral acids, such as hydrochloride, hydrobromide, borate, phosphate, sulphate, hydrogensulphate, hydrogenphosphate, and those with organic acids, such as citrate, benzoate, ascorbate, methylsulphate, naphthalene-2-sulphonate, picrate, fumarate, maleate, malonate, oxalate, succinate, acetate, tartrate, mesylate, tosylate, isethionate, α-ketoglutarate, α-glycerophosphate, glucose-1-phosphate, etc.

The compounds of formula (I) in which Z' and Z" are hydrogen or a ($C_1$-$C_3$)alkyl group are prepared as described in WO 97/01536.

The compounds of formula (I) in which one of Z' and Z" is hydrogen and the other is a hydroxyl, as well as the compounds in which Z' and Z" together represent an oxo group, may be prepared as described in WO 93/11107.

The compounds of formula (I) wherein Z" is hydrogen and Z' and Z each represent independently a non-substituted mono-, di-, or tri-substituted phenyl group are prepared according to the following method:

(a) an aryl-1,2,3,6-tetrahydropyridine of formula (II)

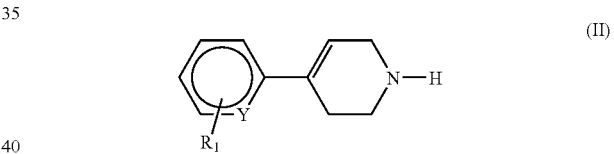

in which Y and $R_1$ are as defined above is allowed to react with an acid of formula (III)

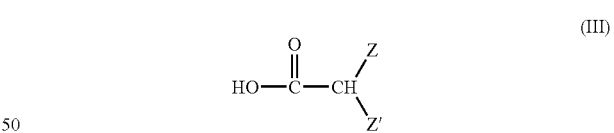

in which Z and Z' are as defined above, or with one of its functional derivatives, (b) the carbonyl intermediate of formula (IV)

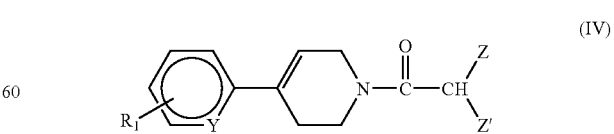

is reduced, and (c) the compound of formula (I) thus obtained is isolated and, optionally, transformed into one of its salts or solvates.

The reaction of step (a) can be conveniently carried out in an organic solvent at a temperature between −10° C. and the reflux temperature of the reaction mixture; preferably the reaction is carried out at a low temperature.

The reaction solvent used is preferably a halogenated solvent such as methylene chloride, dichloroethane, 1,1,1-trichloroethane, chloroform and similar ones, or an alcohol such as methanol or ethanol, but other organic solvents which are compatible with the reagents employed, for example dioxane, tetrahydrofuran or a hydrocarbon such as hexane, may also be employed.

The reaction may conveniently be carried out in the presence of a proton acceptor, for example an alkaline carbonate or a tertiary amine. The free acid, optionally activated (with BOP for example), the anhydride, a mixed anhydride, an activated ester or an acid halide, preferably the chloride or the bromide, may be used as a suitable functional derivative of the acid of formula (III). Amongst the activated esters, the p-nitrophenyl ester is particularly preferred, but the methoxyphenyl, trityl, benzhydryl esters and similar ones are also suitable.

The reduction of step (b) may conveniently be carried out by suitable reducing agents such as aluminium hydrides or a lithium aluminium complex hydride in an inert organic solvent at a temperature between 0° C. and the reflux temperature of the reaction mixture according to usual techniques.

"Inert organic solvent" is understood as meaning a solvent which does not interfere with the reaction. Such solvents are for example ethers, such as diethyl ether, tetrahydrofuran, dioxane or 1,2-dimethoxyethane.

The compound of formula (I) obtained is isolated according to usual techniques and optionally transformed into one of its acid addition salts or, when an acid group is present, the amphoteric character of the compound enables the separation of the salts either with acids or with bases.

The starting amines of formula (II) in which Y is CH are known compounds or may be prepared according to analogous procedures to those used for preparing the known compounds.

The starting amines of formula (II) in which Y is N may be prepared by the reaction of a suitable 2-halopyridine of formula (p)

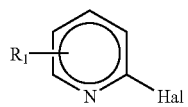

(p)

in which $R_1$ is as defined above and Hal is a halogen atom, with a 1,2,3,6-tetrahydropyridine of formula (q)

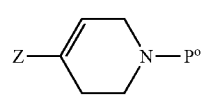

(q)

in which P° represents a protecting group such as a benzyl group for example, and Z represents a substituent which enables nucleophilic substitution of the halogen of the pyridine. Such substituents are for example trialkylstannanes, such as tributylstannane, or Grignard compounds.

The 1,2,3,6-tetrahydropyridine is then deprotected by cleaving the protecting group under suitable conditions.

The acids of formula (III) may be prepared according to the Wittig reaction by the reaction of a suitable benzophenone of formula (r)

(r)

in which Z and Z' are as defined above, with trimethylsulphoxonium iodide/$BF_3$-$Et_2O$ and the oxidation of the intermediate aldehyde of formula (w)

(w)

according to the method described in J. Am. Chem. Soc., 1990. 112(18):6690-6695, to obtain the corresponding acid.

According to another method, the compounds of formula (I) in which Z" is hydrogen may also be prepared by the reaction of an aryl-1,2,3,6-tetrahydropyridine of formula (II)

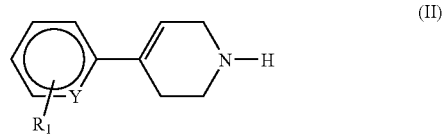

(II)

in which $R_1$ and Y are as defined above, with an aldehyde of formula (w) above in the presence of a reducing agent such as sodium cyanoborohydride, according to known techniques.

The compounds of formula (I), in which $R_1$ is m-trifluoromethyl, Y is CH, Z' and Z" are hydrogen and Z is a naphthyl group substituted with one or two alkoxy groups or with a methylenedioxy group, are prepared as described in EP 0 458 697.

1-(2-naphth-2-ylethyl)-4-(3-trifluoromethylphenyl)-1,2,3,6-tetrahydropyridine and its pharmaceutically acceptable salts and solvates, especially the hydrochloride, may be prepared according to EP 0 101 381.

An advantageous method provides the reaction of 2-(2-bromoethyl)naphthalene and 4-(3-trifluoromethylphenyl)-1,2,3,6-tetrahydropyridine and the isolation preferably of 1-(2-naphth-2-ylethyl)-4-(3-trifluoromethylphenyl)-1,2,3,6-tetrahydropyridine hydrochloride (SR 57746A) which is then crystallised in an ethanol/water mixture by heating and cooling to 5° C. with a cooling gradient of 10° C./hour and a stirring speed of 400 r.p.m., so as to obtain a mixture of the two crystalline forms in a ratio of about 66/34.

The 1-(2-naphth-2-ylethyl)-4-(3-trifluoromethylphenyl)-1,2,3,6-tetrahydropyridine hydrochloride is preferably used in a micro-particulate form, for example in an essentially amorphous form obtained by atomisation, or in a microcrystalline form obtained by micronisation.

The effect of the compounds of formula (I) upon the increase of the levels of TGF-β1 was evaluated with the aid of tests upon the smooth muscle cells, as well as upon the blood levels and the diaphragms in the rat after administration of the representative compounds of the invention.

Both latent TGF-β1 and activated TGF-β1 were determined on the smooth muscle cells by incubation with hydrochloric acid.

In these tests, the representative compounds of formula (I) showed an increase in the levels of TGF-β1.

The anti-apoptotic activity was measured on the same cells vis-à-vis the pro-apoptotic activity of a deprivation in serum or after the addition of toxic compounds such as vincristine or growth factors such as nerve growth factor (NGF) with the aid of a specific ELISA (enzyme-linked immunosorbent assay) determination kit which detects the presence of oligonucleosomes the presence of which inside the cells is a specific marker of programmed cell death (apoptosis), according to the method described by Del Bino G. et al., (Experimental Cell Research, 193, 27, 1991 and 195, 485, 1991) or Darzynkiewicz A et al., (Cytometry, 13, 795, 1992).

In the three cases, the representative compounds of the invention, especially:

1-[2-(3,4-diethylphenyl)ethyl]-4-(3-trifluoromethylphenyl)-1,2,3,6-tetrahydropyridine (compound A);

1-[2-(biphenyl-4-yl)-2-oxoethyl]-4-(3-trifluoromethylphenyl)-1,2,3,6-tetrahydropyridine (compound B);

1-[2-(biphenyl-4-yl)ethyl]-4-(3-trifluoromethylphenyl)-1,2,3,6-tetrahydropyridine (compound C);

1-[2-(6,7-methylenedioxynaphth-2-yl)ethyl]-4-(3-trifluoromethylphenyl)-1,2,3,6-tetrahydropyridine (compound D);

1-[2-(4-cyclohexenylphenyl)ethyl]-4-(3-trifluoromethylphenyl)-1,2,3,6-tetrahydropyridine (compound E)

1-[2-(biphenyl-4-yl)ethyl]-4-(2-trifluoromethylphenyl)-1,2,3,6-tetrahydropyridine (compound F); and 1-(2-naphth-2-ylethyl)-4-(3-trifluoromethylphenyl)-1,2,3,6-tetrahydropyridine (SR 57746)

and their pharmaceutically acceptable salts, inhibit, as a function of time and the dose, the pro-apoptotic effect induced by the deprivation in serum or even by the addition of NGF or vincristine.

Thus, according to a further aspect, the present invention relates to the use of tetrahydropyridines of formula (I), of the advantageous or preferred compounds cited above, or of their pharmaceutically acceptable salts and solvates for the preparation of a medicament for treating diseases treatable by increasing the levels of TGF-β1. Such pathologies are for example diseases linked to an abnormal apoptotic activity, ocular diseases such as cataracts or glaucoma, osteoporosis, bone fractures, epidermal lesions, restenosis, conditions linked to an incorrect proliferation or migration of the smooth muscle cells, inflammations of the respiratory system, asbestosis, silicosis, lupus erythematosus, Goodpasture's syndrome, granulomatosis, eosinophilic granulomatosis, gastric and duodenal ulcers, oesophagitis, enteritis, gastritis, septicaemia, dysfunctions of the haematopoiesis and/or lymphopoiesis, cystic fibrosis.

According to a particularly advantageous aspect, the present invention relates to the use of tetrahydropyridines of formula (I), of the advantageous or preferred compounds cited above, or of their pharmaceutically acceptable salts and solvates for the preparation of medicaments capable of inhibiting apoptosis.

It is by virtue of this anti-apoptotic activity that the compounds of the present invention may be used for the preparation of medicaments for treating cancer and its metastases, infections by antiviruses such as HIV and HTLV 1 and 2 (human immunodeficiency virus and human T lymphocyte virus) and the consequences thereof such as ATL (Adult-cell Leukaemia), leukaemia, myelopathies and arthropathies, hepatites (C, A, B, F), AIDS, immune deficiencies, cell aging, tissue degeneration phenomena, inflammation, cell proliferation, infectious diseases, graft rejection, acute or chronic rheumatoid arthritis, ulcerative colitis, thrombocytopenic purpura, autoimmune erythronoclastic anaemia, juvenile (Type I) diabetes (insulin-dependent), myelodysplasic syndrome, Huntington's disease, prion diseases, ARDS, prostatic hypertrophy, asthma, atherosclerosis and its thrombo-embolic complications, renal diseases, glomerulonephritis, ischemic pathologies such as myocardial infarction, myocardial ischemia, coronary vasospasm, angina and cardiac failure, chronic pancreatitis, auto-immune gastritis, primary biliary cirrhosis.

According to an advantageous aspect, the present invention relates to the use of tetrahydropyridines of formula (I), of one of the advantageous or preferred compounds cited above, or of their pharmaceutically acceptable salts and solvates for the preparation of medicaments capable of treating a disease such as graft rejection or acute or chronic rheumatoid arthritis.

According to the aim of the present invention, "treatment of diseases" is understood as meaning both the treatment and the prevention of the diseases, when this is possible. Thus, for example, when graft rejection is considered, the pharmaceutical compositions may be used in the aim of prevention.

According to a further aspect, the invention relates to a method for increasing circulating and cellular and extracellular levels of TGF-β1.

According to another of its aspects, the present invention relates to a method for inhibiting apoptosis, which comprises the administration to a mammal in need thereof of an effective dose of a compound of formula (I), of one of the advantageous or preferred compounds cited above, or of one of their pharmaceutically acceptable salts and solvates, advantageously SR 57746, or one of its pharmaceutically acceptable salts and solvates.

According to a preferred aspect, SR 57746 and its pharmaceutically acceptable salts and solvates are administered in a micro-particulate form, preferably in a micro-particulate form of the hydrochloride.

The compounds of formula (I), one of the advantageous or preferred compounds cited above or their pharmaceutically acceptable salts and solvates are preferably administered orally.

The amount of active principle to be administered depends upon the degree of advancement of the disease as well as the age and weight of the patient. However, the unit doses generally comprise from 0.25 to 700 mg, advantageously from 0.5 to 300 mg, preferably from 1 to 150 mg, for example between 2 and 50 mg of active principle. These unit doses are normally administered once or more times a day, preferably once to three times per day, the overall dose in man being variable between 0.5 and 1,400 mg per day, for example from 1 to 900 mg per day, advantageously from 2 to 500 mg per day, more conveniently from 2 to 200 mg per day. When the active principle administered is for example SR 57746, the unit dose generally comprises from 0.5 to 10 mg, advantageously from 1 to 5, preferably from 1 to 3 mg, for example 1-1.5-2-2.5-3 mg of active principle. These unit doses are normally administered once or more times per day, preferably once to three times per day, the overall dose in man being variable between 0.5 and 50 mg per day, for example from 1 to 20 mg per day, advantageously from 2 to 10 mg per day.

The doses and amounts above refer to the compounds of formula (I) or to one of the advantageous or preferred compounds cited above, in a non-salified form.

In the pharmaceutical compositions of the present invention for oral administration, the active principle may be administered as unit forms for administration, in a mixture with classical pharmaceutical carriers, to mammals, to animals and to human beings for the treatment of the abovementioned diseases. The suitable unit forms of administration comprise for example tablets, which are optionally scored, gelatine capsules, powders, granules and oral solutions or suspensions.

When a solid composition is prepared in the form of tablets, the main active ingredient is mixed with a pharmaceutical vehicle such as gelatine, starch, lactose, magnesium stearate, talc, gum arabic or analogues thereof. The tablets may be coated with sucrose or other suitable materials or even they may be treated such that they have a sustained or delayed activity and that they continuously release a predetermined amount of the active principle.

A gelatine capsule preparation is obtained by mixing the active ingredient with a diluant and in pouring the mixture obtained into soft or hard gelatine capsules.

A preparation in the form of a syrup or elixir may contain the active ingredient together with a sweetener, preferably an acalorific sweetener, methylparaben and propylparaben as antiseptics, as well as a flavouring agent and a suitable colouring agent.

Powders or granules which may be dispersed in water can contain the active ingredient in a mixture with dispersing agents or wetting agents, or suspension agents, such as polyvinylpyrrolidone, as well as with sweeteners or flavour correctors.

The active principle may also be formulated in the form of microcapsules, optionally with one or more carriers or additives.

In the pharmaceutical compositions according to the present invention, the active principle may also be in the form of an inclusion complex in cyclodextrins, their ethers or their esters. The PREPARATIONS and EXAMPLES below illustrate the invention better.

Preparation 1

40,000 smooth muscle cells isolated from the human aorta (supplier: CLONETICS) are placed, in a 35 mm dish, in a medium containing 2 ml of DMEM (Dulbecco Modified Eagle Medium containing 4.5 g/l of glucose, 3.7 g/l of $NaHCO_3$ and not containing any L-glutamine or Na-pyruvate). 20% v/v of foetal calf serum which was desupplemented for 30 min at 80° C., 4 mM L-glutamine, 50 U/ml of penicillin and 50 µg/ml of streptomycin are added. The cells are left in this medium for a growth period of three days before submitting them to tests according to the examples given further on.

Preparation 2

Dishes containing cells are prepared as described in Preparation 1. Apoptosis is induced by replacing the medium described in Preparation 1 with the same medium containing only 0.2% of foetal calf serum. The effect of the compounds of the invention upon the levels of latent and activated TGF-β1 is measured in the extracellular media after 24 hours of contact with the cells, in comparison with controls (0.2% of foetal calf serum and 20% of foetal calf serum). The activated TGF-β1 is determined directly in the supernatants of the culture, but the latent TGF-β1 is determined after activation. For the activation, 0.5 ml of the supernatant of the culture are incubated in the presence of 0.1 ml of 1M HCl for 10 min. at room temperature. The mixture is then neutralised with 0.1 ml of 0.5 M Hepes buffer which contains 1.2 M NaOH. Determinations of TGF-β1 are carried out with the aid of a specific ELISA test.

Preparation 3

5 Sprague Dawley rats (Iffa Credo, France) of about 280 g were treated every day for three days with the compound to be tested, which was administered orally. 24 hours after the last forced feeding, the rats are anaesthetised. Blood is taken from the abdominal aorta on EDTA, the samples are centrifuged and the supernatants (plasma rich in platelets) are frozen. The diaphragms are also taken, rinsed several times in cold PBS (Phosphate buffered saline) and are centrifuged. After a further ultra-centrifugation the plugs are taken up into PBS and frozen. Determinations of latent and activated TGF-β1 in the plasma and the ground diaphragms are made by using the technique described in PREPARATION 2. The increase in the circulating latent TGF-β1 levels are recorded in the rats treated with the compounds of the invention in comparison with control rats. The increase in the activated TGF-β1 levels in the diaphragms of the rats treated with the compounds of the invention are also recorded.

Preparation 4

Dishes containing the cells are prepared as in PREPARATION 1. Apoptosis is induced by three different methods:
a) by replacing the medium of PREPARATION 1 with the same medium containing only 0.2% of foetal calf serum;
b) by adding increasing doses of NGF (0.01 ng/ml to 100 ng/ml) to the medium described in PREPARATION 1;
c) by adding increasing doses of Vincristin (0.1 pg/ml to 10 ng/ml) to the medium described in PREPARATION 1.

By an ELISA determination test of the mono- and oligo-nucleosomes associated with cytoplasmic histones after washing and cellular lysis, the effects of the compounds of the invention upon the apoptosis are measured after 24 hours of contact with the cells in comparison with the levels of apoptosis obtained in the absence of products (maximum apoptosis level) or in the presence of 20% foetal calf serum (minimum apoptosis level).

EXAMPLE 1

1-(2,2-diphenylethyl)-4-(3-trifluoromethylphenyl)-1, 2,3,6-tetrahydropyridine and its hydrochloride 1a/ 1-(α,α-diphenylacetyl)-4-(3-trifluoromethylphenyl)-1,2, 3,6-tetrahydropyridine.

8 g of α,α-diphenylacetyl chloride in 50 ml of methylene chloride were added dropwise to a mixture of 8 g (0.035 mole) of 4-(3-trifluoromethylphenyl)-1,2,3,6-tetrahydropyridine, 50 ml of methylene chloride and 4.96 ml of triethylamine at the temperature of 0/+5° C. Stirring is effected for one hour at room temperature, the solvent is evaporated off under reduced pressure, the residue is taken up into ethyl ether, washing is effected with a 0.2M aqueous solution of hydrochloric acid, with water, with an aqueous solution of sodium carbonate and then with water. Drying is effected over sodium sulphate, the solvent is evaporated off under reduced pressure. 5 g of the title compound are obtained.

1b/ 1-(2,2-diphenylethyl)-4-(3-trifluoromethylphenyl)-1,2,3,6-tetrahydropyridine and its hydrochloride.

A solution of 5 g (0.012 mole) of the product of the preceding step in 50 ml of ethyl ether is added dropwise to a mixture of 0.7 g of lithium aluminium hydride in 10 ml of ethyl ether at 25° C. Stirring is effected at room temperature for one hour, 5 ml of water are added dropwise. The two phases are separated, the organic phase is dried over sodium sulphate and the solvent is evaporated off under reduced pressure. 1-(2,2-diphenylethyl)-4-(3-trifluoromethylphenyl)-1,2,3,6-tetrahydropyri-dine is thus obtained. The hydrochloride is prepared with the aid of a saturated solution of hydrochloric acid in ethyl ether. Crystallisation is brought about in 150 ml of ethyl acetate. M.p. (hydrochloride) 207-210° C.

EXAMPLE 2

1-[2,2-(4,4'-dichlorodiphenyl)ethyl]-4-(3-trifluoromethylphenyl)-1,2,3,6-tetrahydropyridine and its oxalate 2a/ $\alpha,\alpha$-(4,4'-dichlorodiphenyl)acetaldehyde.

0.75 g (0.025 mole) of 80% sodium hydride in oil is added portionwise to a mixture of 5.5 g (0.025 mole ) of trimethylsulphoxonium iodide in 10 ml of anhydrous tetrahydrofuran. The mixture is heated at 55° C. for 6 hours and 6 g (0.025 mole) of 4,4'-dichlorobenzophenone in 10 ml of anhydrous tetrahydrofuran are added thereto. The mixture is left to stir at 55° C. for one night, poured into water, extracted with ethyl ether, the organic phase is dried over sodium sulphate, and the solvent is evaporated off under reduced pressure. The residue is dissolved in 32 ml of toluene and 3 ml of $BF_3$-$Et_2O$ are added thereto. The mixture is stirred for 2 minutes and is then allowed to stand for 3 minutes. Washing is effected twice with an aqueous solution of sodium bicarbonate, the organic phase is dried over sodium sulphate, and the solvent is evaporated off under reduced pressure. An oil is obtained which is purified by silica gel column chromatography in eluting with a hexane/ethyl acetate mixture=9/1. The title compound is obtained.

2b/ 1-[2,2-(4,4'-dichlorodiphenyl)ethyl]-4-(3-trifluoromethylphenyl)-1,2,3,6-tetrahydropyridine and its oxalate.

1.3 g (0.0045 mole) of the product of the preceding step, 1.2 g (0.0053 mole) of 4-(3-trifluoromethylphenyl)-1,2,3,6-tetrahydropyridine, 21 ml of methanol, 0.8 ml of glacial acetic acid and 0.5 g of anhydrous sodium acetate are mixed at the temperature of 0/+5° C. 0.76 g (0.0121 mole) of sodium cyanoborohydride is added to the mixture at the same temperature, stirring is effected for 1.5 hours at low temperature, and then at room temperature overnight. 5 ml of concentrated hydrochloric acid are added dropwise, stirring is continued for 10 minutes, the methanol is evaporated off and the residue is taken up in an ethyl acetate/dilute aqueous $NH_4OH$ solution mixture. The two phases are separated, the organic phase is dried over sodium sulphate and the solvent is evaporated off under reduced pressure. An oil is obtained which is purified by silica gel column chromatography in eluting with a hexane/ethyl acetate mixture=9/1. The title compound is obtained as a base. The oxalate is prepared with the aid of oxalic acid in isopropanol. M.p. (oxalate) 187-189° C.

EXAMPLE 3

1-[2,2-(3,3'-bistrifluoromethyldiphenyl)ethyl]-4-(3-trifluoromethylphenyl)-1,2,3,6-tetrahydropyridine and its oxalate 3a/ $\alpha,\alpha$(3,3'-bistrifluoromethyldiphenyl)acetaldehyde.

In proceeding as described in Example 2a/, but by using 3,3'-bistrifluoromethylbenzophenone, the title compound is obtained.

3b/ 1-[2,2-(3,3'-bistrifluoromethyldiphenyl)ethyl]-4-(3-trifluoromethylphenyl)-1,2,3,6-tetrahydropyridine and its oxalate.

In proceeding as described in Example 2b/, but by using the product of the preceding step instead of $\alpha,\alpha$-(4,4'-dichlorodiphenyl)acetaldehyde, the title compounds are obtained. M.p. (oxalate) 194-196° C.

EXAMPLE 4

1-[2,2-(4,4'-dimethoxydiphenyl)ethyl]-4-(3-trifluoromethylphenyl)-1,2,3,6-tetrahydropyridine and its hydrochloride 4a/ $\alpha,\alpha$(4,4'-dimethoxydiphenyl)acetaldehyde.

In proceeding as described in Example 2a/, but by using 4,4'-dimethoxybenzophenone, the title compound is obtained.

4b/ 1-[2,2-(4,4'-dimethoxydiphenyl)ethyl]-4-(3-trifluoromethylphenyl)-1,2,3,6-tetrahydropyridine and its hydrochloride.

In proceeding as described in Example 2b/, but by using the product of the preceding step instead of $\alpha,\alpha$-(4,4'-dichlorodiphenyl)acetaldehyde, the title compounds are obtained. M.p. (hydrochloride) 214-216° C.

EXAMPLE 5

1-[2-(4-fluorophenyl)-2-phenylethyl]-4-(3-trifluoromethylphenyl)-1,2,3,6-tetrahydropyridine and its hydrochloride 5a/ $\alpha$-4-fluorophenyl-$\alpha$-phenylacetaldehyde.

In proceeding as described in Example 2a/, but by using 4-fluorobenzophenone, the title compound is obtained.

5b/ 1-[2,2-(4-fluorophenyl)-2-phenylethyl]-4-(3-trifluoromethylphenyl)-1,2,3,6-tetrahydropyridine and its hydrochloride.

In proceeding as described in Example 2b/, but by using the product of the preceding step instead of $\alpha,\alpha$-(4,4'-dichlorodiphenyl)acetaldehyde, the title compounds are obtained. M.p. (hydrochloride) 206-208° C.

EXAMPLE 6

1-(3,3-diphenylpropyl)-4-(3-trifluoromethylphenyl)-1,2,3,6-tetrahydropyridine and its hydrochloride In proceeding as described in Example 1b/ but by using commercial 3,3-diphenylpropionic acid (Aldrich, reference D21,165-6) instead of 2,2-diphenylacetic acid, the title compounds are obtained. M.p. (hydrochloride) 176-178° C.

EXAMPLE 7

1-[2,2-(4,4'-dichlorodiphenyl)ethyl]-4-(6-chloropyrid-2-yl)-1,2,3,6-tetrahydropyridine and its hydrochloride In proceeding as described in Example 2b/ but by using 4-(6-chloropyrid-2-yl)-1,2,3,6-tetrahydropyridine instead of 4-(3-trifluoromethylphenyl)-1,2,3,6-tetrahydropyridine, the title compounds are obtained. M.p. (hydrochloride) 230-232° C.

EXAMPLE 8

1-[2-(3,4-diethylphenyl)ethyl]-4-(3-trifluoromethylphenyl)-1,2,3,6-tetrahydropyridine hydrochloride 8a/ 1-bromo-2-(3,4-diethylphenyl)ethane.

A mixture of 4.4 g (0.033 mole) of 3,4-diethylbenzene, 50 ml of methylene chloride, 8,8 g (0.044 mole) of bromoacetyl bromide is cooled to 0-5° C. and 5.0 g (0.037 mole) of aluminum trichloride are added thereto. The mixture is stirred at 0-5° C. for one hour and is then allowed to stand overnight at room temperature. It is poured into a water/ice mixture, extracted with methylene chloride, the organic phase is dried over sodium sulphate and the solvent is evaporated off under reduced pressure. 2.9 g (0.011 mole) of the oil thus obtained are mixed with 6 ml (0.079 mole) of trifluoroacetic acid and 6.7 ml (0.057 mole) of triethylsilane and the mixture is heated at 80° C. for 4 hours. A saturated aqueous solution of sodium bicarbonate is then added up to basic pH, extraction is effected with ethyl ether, the organic phase is dried over sodium sulphate and the solvent is evaporated off under reduced pressure. The crude oil thus obtained is purified by silica gel column chromatography in eluting with cyclohexane. The title compound is obtained.

8b/ 1-[2-(3,4-diethylphenyl)ethyl]-4-(3-trifluoromethylphenyl)-1,2,3,6-tetrahydropyridine hydrochloride.

A mixture of 2.6 g (0.001 mole) of 4-(3-trifluoromethylphenyl)-1,2,3,6-tetrahydropyridine, 60 ml of butanol, 4.1 g (0.025 mole) of grated anhydrous potassium carbonate and 2.6 g (0.00113 mole) of the product of the preceding step is refluxed for 5 hours. The solvent is evaporated off under reduced pressure, it is taken up into ethyl acetate, washed with water, drying is effected over sodium sulphate and the solvent is evaporated off under reduced pressure. The hydrochloride of the oil thus obtained is prepared by treatment with a saturated solution of hydrochloric acid in isopropanol. 1.6 g of the title compound are obtained M.p. 220-222° C.

EXAMPLE 9

1-[2-(3-methyl-4-pentylphenyl)ethyl]-4-(3-trifluoromethylphenyl)-1,2,3,6-tetrahydropyridine and 1-[2-(4-methyl-3-pentylphenyl)ethyl]-4-(3-trifluoromethylphenyl)-1,2,3,6-tetrahydropyridine and their oxalates 9a/ 1-methyl-2-pentylbenzene.

4.7 g (0.035 mole) of phthalic aldehyde are added dropwise to a solution of 50 ml (0.1 mole) of a 2M n-butylmagnesium chloride solution in THF under nitrogen atmosphere. The mixture spontaneously heats up to 40-45° C. Stirring is effected at room temperature for one hour, the mixture is poured into a saturated ammonium chloride solution, extracted with ethyl ether, washed with water, drying is effected over sodium sulphate and the solvent is evaporated off under reduced pressure. The oil thus obtained is purified by silica gel column chromatography in eluting with a cyclohexane/ethyl acetate mixture=7/3. The product having the highest Rf is isolated. 2.0 g of oil are obtained. The crude reaction mixture is dissolved in 25 ml of ethanol and 1 ml of concentrated sulphuric acid and 0.15 g of 10% Pd/C are added thereto. Hydrogenation is carried out at room temperature for 7 hours. The catalyst is filtered off, the solvent is evaporated off under reduced pressure and the residue is taken up into ethyl acetate. The mixture is washed with an aqueous solution of sodium bicarbonate, dried and the solvent is evaporated off under reduced pressure. 1.35 g of the title compound are obtained.

9b/ 1-bromo-2-(3-methyl-4-pentylphenyl)ethane and 1-bromo-2-(4-methyl-3-pentylphenyl)ethane.

A mixture of 1.17 g (0.0054 mole) of the product of the preceding step, 0.62 ml (0.0072 mole) of bromoacetyl bromide is cooled to 0-5° C. and 0.81 g (0.006 mole) of aluminium trichloride is added thereto. Stirring is effected at 0-5° C. for one hour and then 4 hours at room temperature. The mixture is poured into ice, the two phases are separated, the organic phase is washed with water, dried and the solvent is evaporated off under reduced pressure. The residue is dissolved in 2.9 ml of trifluoroacetic acid and 3.1 ml (0.0267 mole) of triethylsilane are added thereto and the mixture is heated at 80° C. for 5 hours. It is poured into an aqueous solution of sodium bicarbonate and extracted with ethyl ether, washed with water and the drying is effected over sodium sulphate. A mixture of the title compounds is obtained.

9c/ 1-[2-(3-methyl-4-pentylphenyl)ethy]-4-(3-trifluoromethylphenyl)-1,2,3,6-tetrahydropyridine and 1-[2-(4-methyl-3-pentylphenyl)ethyl]-4-(3-trifluoromethylphenyl)-1,2,3,6-tetrahydropyridine and their oxalates.

A mixture of 0.7 g (0.0031 mole) of 4-(3-trifluoromethylphenyl)-1,2,3,6-tetrahydropyridine, 16 ml of butanol, 0.9 g (0.0065 mole) of grated anhydrous potassium carbonate and the product obtained in the preceding step (0.0054 mole theoretical) is refluxed for 6 hours. The solvent is evaporated off under reduced pressure, the residu is taken up into ethyl acetate, washed with water, drying is effected over sodium sulphate and the solvent is evaporated off under reduced pressure. The oil thus obtained is purified by silica gel column chromatography in eluting with a cyclohexane/ethyl acetate mixture=7/3. Two products having similar Rfs are isolated. The product having the highest Rf corresponds to 1-[2-(3-methyl-4-pentylphenyl)ethyl]-4-(3-trifluoromethylphenyl)-1,2,3,6-tetrahydropyridine. The oxalate is prepared in acetone. 0.12 g of product is obtained. M.p. 140-143° C. The product having the lowest Rf corresponds to the 1-[2-(4-methyl-3-pentylphenyl)ethyl]-4-(3-trifluoromethylphenyl)-1,2,3,6-tetrahydropyridine isomer. The oxalate is prepared in acetone. Crystallisation of the product is brought about in acetone. 0.08 g of product is obtained. M.p. 167-169° C.

EXAMPLE 10

1-[2-(3,4-diethylphenyl)ethyl]-4-(6-chloropyrid-2-yl)-1,2,3,6-tetrahydropyridine hydrochloride 10a/(1-benzyl-1,2,3,6-tetrahydropyrid-4-yl)tributylstannane.

A mixture of 15.85 g (0.0837 mole) of 1-benzyl-4-piperidone in 140 ml of anhydrous dimethoxyethane and 25 g (0.0837 mole) of trisilidrazine in 140 ml of anhydrous dimethoxyethane is stirred at room temperature for 3 hours. The solvent is evaporated off under reduced pressure. The residue is taken up into 420 ml of anhydrous hexane and 420 ml of anhydrous tetramethylethylenediamine are added thereto. The mixture is cooled to −78° C. and 156 ml of n-butyllithium (0.25 mole) (1.6 M solution in hexane) are added dropwise thereto. After about 30 minutes the temperature is allowed to attain 0° C. and stirring is effected for 15 minutes. 45 ml (0.167 mole) of tributylstannyl chloride are then added to the reaction mixture. After 1 hour, a water/ice mixture is added with extreme caution. Extraction is carried out with ethyl ether, the organic phase is washed with water, drying is effected over sodium sulphate and the solvent is evaporated off under reduced pressure. 70 g of crude product are obtained which are purified by silica gel column chromatography in eluting with a cyclohexane/ethyl acetate mixture=95/5. The title compound is obtained as an oil.

$^1$H-NMR (CDCl$_3$)-δ (ppm): 0.84 (9H; m: CH$_3$); 1.19-1.58 (18H; m: CH$_2$-chain); 2.31 (2H; m); 2.53 (2H; m); 3.02 (2H; m); 3.56 (2H; s: benzylic methylene); 5.76 (1H; m*); 7.18-7.41 (5H; m: arom.) * side bands $^3$Jcis($^1$H-$^{117}$Sn) and $^3$Jcis($^1$H-$^{119}$Sn).

10b/ 1-benzyl-4-(6-chloropyrid-2-yl)-1,2,3,6-tetrahydropyridine.

18.5 g (0.04 mole) of the compound of the preceding step are dissolved in 200 ml of anhydrous dimethylfonnamide under nitrogen atmosphere. 11.8 g (0.08 mole) of 2,6-dichloropyridine, 0.64 g of Pd(II) (Ph$_3$P)$_2$Cl$_2$, 4.38 g (0.04 mole) of tetraethylammonium chloride and 2.76 g (0.02 mole) of potassium carbonate are added to the solution. The mixture is heated at 110° C. for 6 hours and is then poured into 100 ml of a 5% sulphuric acid solution. Extraction is carried out with ethyl ether, ammonium hydroxide is added to the aqueous phase up to basic pH and extraction is carried out with ethyl acetate. The combined organic phases are dried over sodium sulphate and the solvent is evaporated off under reduced pressure. The residue is purified by silica gel column chromatography in eluting with a cyclohexane/ethyl acetate mixture=1/1. The title compound is obtained. M.p. 100-102° C.

10c/ 4-(6-chloropyrid-2-yl)-1,2,3,6-tetrahydropyridine hydrochloride.

A solution of 7.0 g (0.024 mole) of the compound of the preceding step in 110 ml of dichloroethane is cooled to 0-5° C. and 5.8 ml (0.054 mole) of chloroethyl chloroformate are added thereto. Stirring is effected for 5 minutes and then refluxing is effected for 1.5 hours. The solvent is evaporated off under reduced pressure, the residue is taken up in 100 ml of methanol and heating under reflux is effected for 1 hour. The solvent is evaporated off, the residue is taken up in isopropanol and the solid is filtered off. The title compound is obtained which is crystallised in 90% ethanol. M.p. 305-307° C.

10d/ 1-[2-(3,4-diethylphenyl)ethyl]-4-(6-chloropyrid-2-yl)-1,2,3,6-tetrahydropyridine hydrochloride.

In proceeding as described in Example 8b/ but by using the product of the preceding step instead of 4-(3-trifluoromethylphenyl)-1,2,3,6-tetrahydropyridine, the title compound is obtained. M.p. 234-236° C.

EXAMPLES 11-20

In proceeding as described in Example 9 but by using the appropriate magnesium halide, the following compounds are obtained:

1-[2-(3-ethyl-4-methylphenyl)ethyl]-4-(3-trifluoromethylphenyl)-1,2,3,6-tetrahydropyridine—Ex. 11
1-[2-(4-ethyl-3-methylphenyl)ethyl]-4-(3-trifluoromethylphenyl)-1,2,3,6-tetrahydropyridine—Ex. 12
1-[2-(3-ethyl-4-propylphenyl)ethyl]-4-(3-trifluoromethylphenyl)-1,2,3,6-tetrahydropyridine—Ex. 13
1-[2-(4-ethyl-3-propylphenyl)ethyl]-4-(3-trifluoromethylphenyl)-1,2,3,6-tetrahydropyridine—Ex. 14
1-[2-(3-butyl-4-methylphenyl)ethyl]-4-(3-trifluoromethylphenyl)-1,2,3,6-tetrahydropyridine—Ex. 15
1-[2-(4-butyl-3-methylphenyl)ethyl]-4-(3-trifluoromethylphenyl)-1,2,3,6-tetrahydropyridine—Ex. 16
1-[2-(3-isobutyl-4-methylphenyl)ethyl]-4-(3-trifluoromethylphenyl)-1,2,3,6-tetrahydropyridine—Ex. 17
1-[2-(4-isobutyl-3-methylphenyl)ethyl]-4-(3-trifluoromethylphenyl)-1,2,3,6-tetrahydropyridine—Ex. 18
1-[2-(3-isobutyl-4-ethylphenyl)ethyl]-4-(3-trifluoromethylphenyl)-1,2,3,6-tetrahydropyridine—Ex.19
1-[2-(4-isobutyl-3-ethylphenyl)ethyl]-4-(3-trifluoromethylphenyl)-1,2,3,6-tetrahydropyridine—Ex. 20

EXAMPLE 21

1-[2-(6-methyl-3-biphenylyl)ethyl]-4-(3-trifluoromethylphenyl)-1,2,3,6-tetrahydropyridine In proceeding as described in Example 9 but by using phenyllithium instead of n-butylmagnesium chloride, the title compound is obtained.

EXAMPLE 22

1-[2-(3'-chlorobiphenyl-4-yl)-2-oxoethyl]-4-(3-trifluoromethylphenyl)-1,2,3,6-tetrahydropyridine hydrochloride 22a/ 1-bromo-2-(3'-chlorobiphenyl-4-yl)ethanone.

A mixture of 5 g (0.026 mole) of 3-chlorobiphenyl, 50 ml of methylene chloride, 6.95 g (0.034 mole) of bromoacetyl bromide is cooled to 0-5° C. and 4 g (0.030 mole) of aluminium trichloride are added thereto. Stirring is effected for 1 hour at 5° C. and then 4 hours at room temperature. The mixture is poured into a water/ice mixture, extracted with methylene chloride, the organic phase is washed with a 1N HCl solution, drying is effected over sodium sulphate and the residu is evaporated under reduced pressure. 4.5 g of the title compound are obtained. M.p. 63-65° C.

22b/ 1-[2-(3'-chlorobiphenyl-4-yl)-2-oxoethyl]-4-(3-trifluoromethylphenyl)-1,2,3,6-tetrahydropyridine hydrochloride.

A mixture of 0.4 g (0.013 mole) of the product of the preceding step, 2.95 g (0.013 mole) of 4-(3-trifluoromethylphenyl)-1,2,3,6-tetrahydropyridine, 80 ml of ethanol and 2.32 g (0.0167 mole) of grated anhydrous potassium carbonate is refluxed for 1 hour. The salts are removed by filtering and the solution is acidified by the addition of a saturated solution of hydrochloric acid in ethanol. Concentration is carried out under reduced pressure until about 40 ml and the residue is allowed to stand overnight at 5° C. The precipitate is filtered off, washed with water and then with isopropanol. 4.9 g of the title compound are obtained. M.p. 217-220° C.

EXAMPLE 23

1-[2-(2'-chlorobiphenyl-4-yl)-2-oxoethyl]-4-(3-trifluoromethylphenyl)-1,2,3,6-tetrahydropyridine hydrochloride In proceeding as described in Example 22 but by using 2-chlorobiphenyl instead of 3-chlorobiphenyl, the title compound is obtained. M.p. 200-202° C. (crystallised in isopropanol).

EXAMPLE 24

1-[2-(4-chlorobiphenyl-4-yl)-2-oxoethyl]-4-(3-trifluoromethylphenyl)-1,2,3,6-tetrahydropyridine hydrochloride In proceeding as described in Example 22 but by using 4-chlorobiphenyl instead of 3-chlorobiphenyl, the title compound is obtained. M.p. 210-215° C.

EXAMPLE 25

1-[2-(4-isobutylphenyl)-2-oxoethyl]-4-(3-trifluoromethylphenyl)-1,2,3,6-tetrahydropyridine hydrochloride In proceeding as described in Example 22 but by using 4-isobutylbenzene instead of 3-chlorobiphenyl, the title compound is obtained. M.p. 224-228° C. (crystallised in isopropanol).

EXAMPLE 26

1-[2-(4-phenoxyphenyl)-2-oxoethyl]-4-(3-trifluoromethylphenyl)-1,2,3,6-tetrahydropyridine hydrochloride In proceeding as described in Example 22 but by using diphenyl ether instead of 3-chlorobiphenyl, the title compound is obtained. M.p. 205-210° C.

EXAMPLE 27

1-[2-(4-cyclohexylphenyl)-2-oxoethyl]-4-(3-trifluoromethylphenyl)-1,2,3,6-tetrahydropyridine hydrochloride In proceeding as described in Example 22 but by using cyclohexylbenzene instead of 3-chlorobiphenyl, the title compound is obtained. M.p. 209-213° C. (crystallised in isopropanol).

EXAMPLE 28

1-[2-(4'-fluorobiphenyl-4-yl)-2-oxoethyl]-4-(3-trifluoromethylphenyl)-1,2,3,6-tetrahydropyridine hydrochloride In proceeding as described in Example 22 but by using 4-fluorobiphenyl instead of 3-chlorobiphenyl, the title compound is obtained. M.p. 123-125° C. (crystallised in isopropanol).

EXAMPLE 29

1-[2-(biphenyl-4-yl)-2-oxoethyl]-4-(3-trifluoromethylphenyl)-1,2,3,6-tetrahydropyridine hydrochloride In proceeding as described in Example 22 but by using biphenyl instead of 3-chlorobiphenyl, the title compound is obtained. M.p. 145-147° C. (base); M.p. 240-243° C. (hydrochloride).

EXAMPLE 30

1-[2-(4-n-butylphenyl)-2-oxoethyl]-4-(3-trifluoromethylphenyl)-1,2,3,6-tetrahydropyridine hydrochloride In proceeding as described in Example 22 but by using 4-n-butylbenzene instead of 3-chlorobiphenyl, the title compound is obtained. M.p. 218-221° C.

EXAMPLE 31

1-[2-(4-t-butylphenyl)-2-oxoethyl]-4-(3-trifluoromethylphenyl)-1,2,3,6-tetrahydropyridine hydrochloride In proceeding as described in Example 22 but by using 4-t-butylbenzene instead of 3-chlorobiphenyl, the title compound is obtained. M.p. 97-99° C. (base).

EXAMPLE 32

1-[2-(3,4-diethylphenyl)-2-oxoethyl]-4-(3-trifluoromethylphenyl)-1,2,3,6-tetrahydropyridine hydrochloride In proceeding as described in Example 22 but by using 3,4-diethylbenzene instead of 3-chlorobiphenyl, the title compound is obtained. M.p. 232-234° C.

EXAMPLE 33

1-[2-(2'-trifluoromethylbiphenyl-4-yl)-2-oxoethyl]-4-(3-trifluoromethylphenyl)-1,2,3,6-tetrahydropyridine hydrochloride 33a/ 2-(4-bromophenyl)-2,2-dimethoxyethane.

A mixture of 2 g (0.01 mole) of 4-bromoacetophenone, 5.6 ml of trimethyl orthoformate, 5.6 ml of methanol and 0.67 g of Amberlite® IR 120 is refluxed for three hours. After cooling, it is filtered through, Celite® and the filtered solution is evaporated. 2.4 g of the title product are obtained as an oil.

33b/ 2,2-dimethoxy-2-(2'-trifluoromethylbiphenyl-4-yl) ethane.

A mixture of 4.9 g (14 mmole) of the product of the preceding step, 2.45 g (16 mmole) of 2-trifluoromethylbenzeneboronic acid, 63 mg (0.28 mmole) of palladium acetate, 4.84 g (35 mmole) of potassium carbonate and 4.5 g (14 mmole) of tetrabutylammonium bromide in 19 ml of water is stirred at 70° C. for 1 hour. It is left to cool and it is extracted with ethyl acetate. The organic phase is dried over sodium sulphate, filtered and the solvent is evaporated under reduced pressure. The title compound is obtained as an oil.

33c/ 4-(2-trifluorophenyl)acetophenone.

A solution of 4 ml of trifluoroacetic acid and 4 ml of water is added to a solution of 4.6 g (0.0105 mole) of the product of the preceding step in 4 ml of methylene chloride at 0° C. The mixture is stirred at room temperature for 2 hours, is poured into water and extracted with methylene chloride. The organic phase is dried, filtered and the solvent is evaporated off under reduced pressure. The crude is purified by silica gel column chromatography in eluting with a cyclohexane/ethyl acetate mixture=9/1. 1.97 g of the title product are obtained.

33d/ α-bromo-4-(2-trifluoromethylphenyl)acetophenone.

0.38 ml (7.5 mmole) of bromine is added dropwise to a solution of 1.97 g (7.5 mmole) of the product of the preceding step in 5.4 ml of methanol, at a temperature of 0° C. Stirring is effected at room temperature for 3 hours, the solvent is evaporated and the residue is taken up into water and extracted with ethyl acetate. The organic phase is dried over sodium sulphate, filtered and the solvent is evaporated off under reduced pressure. The title product is obtained as an oil.

33e/ 1-[2-(2'-trifluoromethylbiphenyl-4-yl)-2-oxoethyl]-4-(3-trifluoromethylphenyl)-1,2,3,6-tetrahydropyridine hydrochloride.

A mixture of 0.74 g (0.0028 mole) of 4-(3-trifluoromethylphenyl)-1,2,3,6-tetrahydropyridine, 14 ml of ethanol and 1.27 g (0.0092 mole) of grated anhydrous potassium carbonate is refluxed for 1 hour. A solution of 1.2 g (0.0035 mole) of the oil of the preceding step in 3 ml of ethanol is added thereto and the mixture is left under reflux for 30 minutes. The salts are removed by filtration, and the solution is acidified by the addition of a 1 M aqueous hydrochloric acid solution. The solvent is evaporated off under reduced pressure, extraction is carried out with chloroform, and the organic phase is dried over sodium sulphate, filtered and the solvent is evaporated off under reduced pressure. The base is released with the aid of a concentrated solution of ammonia, is extracted with ethyl acetate, and the product is purified by silica gel column chromatography in eluting with a cyclohexane/ethyl acetate mixture=8/2. The title compound is obtained. The hydrochloride is prepared with the aid of a saturated solution of hydrochloric acid in isopropanol. M.p. 195-197° C.

EXAMPLE 34

1-[2-(3'-trifluoromethylbiphenyl-4-yl)-2-oxoethyl]-4-(3-trifluoromethylphenyl)-1,2,3,6-tetrahydropyridine hydrochloride In proceeding as described in Example 33 but by using 3-trifluoromethyl-benzeneboronic acid instead of 2-trifluoromethylbenzeneboronic acid in step 33b/, the title compound is obtained. M.p. 232-234° C.

EXAMPLE 35

1-[2-(4'-trifluoromethylbiphenyl-4-yl)-2-oxoethyl]-4-(3-trifluoromethylphenyl)-1,2,3,6-tetrahydropyridine hydrochloride In proceeding as described in Example 33 but by using 4-trifluoromethylbenzene-boronic acid instead of 2-trifluoromethylbenzeneboronic acid in step 33b/, the title compound is obtained. M.p. 245-247° C.

EXAMPLE 36

A mixture of 12.5 g of 2-(2-bromoethyl)naphthalene, 14 g of 4-(3-trifluoromethylphenyl)-1,2,3,6-tetrahydropyridine hydrochloride, 4.34 g of sodium hydroxide, 135 ml of water and 95 ml of 95% ethanol is heated for 5 hours under reflux, and the reaction mixture is then left to cool overnight to room temperature. The mixture is cooled to below 25° C., and then is filtered, the product thus isolated is washed with water and then dried in vacuo at 50° C. 1-[2-(2-naphthyl)ethyl]-4-(3-trifluoromethylphenyl)-1,2,3,6-tetrahydropyridine base is thus obtained in a yield of 90% calculated on the starting 4-(3-trifluoromethylphenyl)-1,2,3,6-tetrahydropyridine hydrochloride.

EXAMPLE 37

A mixture of 19.5 g of crude 1-[2-(2-naphthyl)ethyl]-4-(3-trifluoromethylphenyl)-1,2,3,6-tetrahydropyridine hydrochloride, 95 ml of absolute ethanol and 4.65 ml of 37% hydrochloric acid is heated under reflux with stirring until complete dissolution, and is then left to cool whilst the stirring is continued. When the first crystals start to form (about 63° C.), the stirring is stopped and the reaction mixture is maintained at 0-5° C. overnight. After filtering, the product is swollen twice in 30 ml of absolute ethanol, and then dried overnight at 40° C. in vacuo.

Under these conditions, 12.8 g of Form I of 1-[2-(2-naphthyl)ethyl]-4-(3-trifluoromethylphenyl)-1,2,3,6-tetrahydropyridine hydrochloride are obtained.

The differential calorimetric analysis of Form I obtained in this preparation shows a solid-solid transition temperature of 148-149° C.

a transition enthalpy of 26.4 J/g.

EXAMPLE 38

A mixture of 70 g of crude 1-[2-(2-naphthyl)ethyl]-4-(3-trifluoromethylphenyl)-1,2,3,6-tetrahydropyridine hydrochloride and 1 l of absolute ethanol is refluxed in a Mettler RC1 calorimetric reactor equipped with an impeller of 8 cm in diameter until complete dissolution of the product. The solution thus obtained is cooled with a cooling rate of 80° C. per hour and a stirring speed of 500 r.p.m.to 10° C. The precipitate thus obtained is filtered and dried overnight at 45° C. in vacuo.

Under these conditions, Form II of 1-[2-(2-naphthyl)ethyl]-4-(3-trifluoromethylphenyl)-1,2,3,6-tetrahydropyridine hydrochloride is obtained.

The differential calorimetric analysis of Form II obtained in this preparation shows a solid-solid transition temperature of 153-155° C.

a transition enthalpy of 24.1 J/g.

EXAMPLE 39

A mixture of 2 g of 1-[2-(2-naphthyl)ethyl]-4-(3-trifluoromethylphenyl)-1,2,3,6-tetrahydropyridine hydrochloride and 50 ml of dimethylsulphoxide is refluxed until complete dissolution, it is left to cool overnight, and then the crystalline product is recovered and dried in vacuo at 45° C. overnight.

Under these conditions, Form III of 1-[2-(2-naphthyl)ethyl]-4-(3-trifluoromethylphenyl)-1,2,3,6-tetrahydropyridine hydrochloride is obtained.

The differential calorimetric analysis of Form III obtained in this preparation shows
a solid-solid transition temperature of 141-142° C.
a transition enthalpy of 17.6 J/g.

EXAMPLE 40

A mixture of 100 g of 1-[2-(2-naphthyl)ethyl]-4-(3-trifluoromethylphenyl)-1,2,3,6-tetrahydropyridine hydrochloride in 1 l of an ethanol/water mixture 90/10 is refluxed with stirring until complete dissolution of the product. The solution thus obtained is cooled from the reflux temperature to 5° C. under impeller stirring at 400 r.p.m. at a cooling speed of 10° C./hour. The crystalline product thus obtained is filtered and dried at 45° C. in vacuo overnight.

Under these conditions, 1-[2-(2-naphthyl)ethyl]-4-(3-trifluoromethylphenyl)-1,2,3,6-tetrahydropyridine hydrochloride is obtained as a mixture of Form I/Form III, in a ratio of 65.7/34.3.

The differential calorimetric analysis of Form I/III obtained in this preparation shows a thermogram which shows only the two characteristic peaks corresponding to Forms I and III.

EXAMPLE 41

A solution of 3 g of 1-[2-(2-naphthyl)ethyl]-4-(3-trifluoromethylphenyl)-1,2,3,6-tetrahydropyridine hydrochloride in 300 ml of ethanol is atomised in a "Büchi mini Spray Dryer" apparatus according to the principal of atomisation by parallel current pipe, in regulating the flow rate of the pump, the suction, the heating and the current flow so as to have an entry temperature of 172° C., an exit temperature of 107° C. and a depression of 40 mbar. Under these conditions, a wide DSC monopeak product is obtained with the maximum at 145° C. The particles obtained are spherical and the very homogenous population does not exceed 5 micrometres in average size.

EXAMPLE 42

24 kg of 1-[2-(2-naphthyl)ethyl]-4-(3-trifluoromethylphenyl)-1,2,3,6-tetrahydropyridine hydrochloride—Form I/III, described in Example 40, are introduced into the micronisation chamber (200 mm diameter) of an Alpine 200 AS microniser at a speed of 25 kg/hour and at a working pressure of 6.5 bars and the product thus micronised is recovered in a filter sleeve. A micronised product is thus obtained which has a particle distribution according to which the whole of the particles has a size of less than 20 micrometres and 85% of the particles have a size of less than 10 micrometres.

The differential calorimetric analysis of the micronised product thus obtained shows that the transition temperatures are not affected by micronisation. Said transitions are of the solid-solid type. The compound degrades before melting, which starts at 250° C.

EXAMPLE 43

A pharmaceutical composition which contains, as active principle, 1-[2-(2-naphthyl)ethyl]-4-(3-trifluoromethylphenyl)-1,2,3,6-tetrahydropyridine hydrochloride Form I/III (micronised) according to Example 42 above:

| | |
|---|---|
| Active principle | 2.192 mg |
| Corn Starch | 141.208 mg |
| Microcrystalline Cellulose | 26.000 mg |
| Anhydrous colloidal Silica | 0.200 mg |
| Magnesium Stearate | 0.400 mg |

The active principle is sieved at 0.2 mm, and then premixed with the excipients. This mixture is sieved at 0.315 mm, remixed, and then sieved again at 0.315 mm. After a final mixing, the composition is introduced into gelatine capsules No. 3, at the rate of 170 mg of the composition containing an amount of 1-[2-(2-naphthyl)ethyl]-4-(3-trifluoromethylphenyl)-1,2,3,6-tetrahydropyridine hydrochloride—Form I/III which corresponds to 2 mg of 1-[2-(2-naphthyl)ethyl]-4-(3-trifluoromethylphenyl)-1,2,3,6-tetrahydropyridine base.

EXAMPLE 44

Dishes containing cells are prepared as in PREPARATION 1. The levels of TGF-$\beta$1 are measured as described in PREPARATION 2. The levels of activated TGF-$\beta$1 are measured in the extracellular media in the presence of SR 57746A after 1, 3, 14, 24 and 48 hours and 7 days of contact with the cells, in comparison with the controls (0.2% foetal calf serum and 20% foetal calf serum) by the method described in PREPARATION 2. SR 57746 induces a significant increase in the levels of activated TGF-$\beta$1 in the extracellular media after 14 hours of contact with the cells.

EXAMPLE 45

Dishes containing cells are prepared as in PREPARATION 1 and apoptosis is induced as in PREPARATION 4 according to method a). The anti-apoptotic effects of SR 57746 and compounds A, B, C, D, E and F are measured after 1, 3, 14, 24, 48 hours and 7 days of contact with the cells in comparison with the controls (0.2% foetal calf serum and 20% foetal calf serum) by the method described in PREPARATION 4.

The compounds tested significantly inhibit the apoptosis induced by deprivation of serum after 24 hours of contact with the cells and for 7 days at least.

EXAMPLE 46

Dishes containing cells are prepared as in PREPARATION 1. Apoptosis is induced according to method b) of PREPARATION 4. The apoptosis levels are measured after 24 hours of contact with the cells by the method described in PREPARATION 4; the same controls as in PREPARATION 4 are used. SR 57746 as well as compounds A, B, C, D, E and F significantly inhibit the pro-apoptotic effect of NGF.

EXAMPLE 47

Dishes containing cells are prepared as described in PREPARATION 1. Apoptosis is induced according to method c) of PREPARATION 4. The levels of apoptosis are measured after 24 hours of contact with the cells by the method described in PREPARATION 4; the same controls as in PREPARATION 4 are used. SR 57746 and compounds A, B, C, D, E and F significantly inhibit the proapoptotic effect of vincristine.

EXAMPLE 48

1-1-[2-(6,7-methylenedioxynaphth-2-yl)ethyl]-4-[3-trifluoromethylphenyl)-1,2,3,6-tetrahydropyridine hydrochloride 1.1 g (0.0048 mole) of 2-(6,7-dimethoxynaphth-2-yl) acetic acid, 20 ml of methylene chloride, 2 ml (0.0144 mole) of triethylamine, 1.35 g (0.0048 mole) of 4-(3-trifluoromethylphenyl)-4-piperidinol and 2.15 g (0.0048 mole) of BOP are stirred at room temperature. Washing is effected with a 1 N HCl solution, and then with a saturated solution of NaHCO$_3$ and then with water. Drying is effected over sodium sulphate and the solvent is evaporated off under reduced pressure. 1.5 g of the oil thus obtained are dissolved in 18 ml of THEF. The mixture is heated at reflux and a solution of 0.97 ml (0.0102 mole) of dimethylsulphide/borane in 12 ml of THF is added dropwise thereto. The mixture is refluxed for 4 hours, cooled to 0° C. and 15 ml of methanol are added. It is heated again at reflux for 30 min, and then evaporated under reduced pressure. The residue is taken up into ethyl acetate, washed with water, dried over sodium sulphate and evaporated under reduced pressure. The oil obtained is dissolved in 22 ml of glacial acetic acid, and 1,2 ml of concentrated sulphuric acid are added thereto, and the mixture is heated at 60° C. for 4 hours. It is poured into an ice/NaOH mixture and is extracted with ethyl acetate. The hydrochloride is prepared with the aid of isopropanol saturated with HCl in obtaining the title compound M.p. 277-280° C.

EXAMPLE 49

49a/ 4-(2-trifluoromethylphenyl)-1,2,3,6-tetrahydropyridine hydrochloride.

A mixture of 2 g (0.0071 mole) of 4-(2-trifluoromethylphenyl)-4-piperidinol (prepared from benzylpiperidone, 2-bromo-1-trifluoromethylbenzene and magnesium and successive hydrogenation), 12 ml of glacial acetic acid and 3 ml of concentrated sulphuric acid is heated at 100° C. for 2 hours. It is poured into an ice/NaOH mixture and is extracted with methylene chloride. The organic phase is dried and evaporated under reduced pressure. The hydrochloride is prepared with the aid of isopropanol saturated with hydrochloric acid. M.p. 213-215° C.

49b/ 1-[2-(biphenyl-4-yl)ethyl]-4-(2-trifluoromethylphenyl)-1,2,3,6-tetrahydropyridine hydrochloride.

In proceeding as described in Example 8b but by using the product of the preceding step instead of 4-(3-trifluoromethylphenyl)-1,2,3,6-tetrahydropyridine and 1-bromo-2-biphenylylethane instead of the product of step 8a, the title compound is obtained. M.p. 273-275° C.

EXAMPLE 50

1-[2-(4-cyclohexenylphenyl)ethyl]-4-(3-trifluoromethylphenyl)-1,2,3,6-tetrahydropyridine hydrochloride A mixture of 1 g (0.005 mole) of 2-(4-bromophenyl) ethanol, 0.7 g (0.0055 mole) of 1-cyclohexeneboronic acid, 25 mg of palladium acetate, 1.73 g (0.0012 mole) of potassium carbonate and 1.61 g (0.005 mole) of tetrabutylammonium bromide in 7 ml of water is stirred at 70° C. for 3 hours. It is left to cool and is extracted with ethyl acetate. The organic phase is dried over sodium sulphate, filtered and the solvent is evaporated under reduced pressure. The reaction crude is purified by silica gel column chromatography, in eluting with a cyclohexane/ethyl acetate mixture=7/3. The title compound is obtained as an oil. A solution of 1.35 g (6.67 mmoles) of the product of the preceding step, 0.93 ml (6.67 moles) of mesyl chloride in 0.5 ml of methylene chloride, is cooled to 0.5° C. The mixture is stirred at 0° C. for 30 minutes and then overnight at room temperature. The mixture is poured into water and is extracted with methylene chloride. The organic phase is dried and the solvent is evaporated off under reduced pressure. The residue is taken up into 8 ml of isopropanol, and 0.64 ml (4.6 mmoles) of triethylamine and 0.45 g (1.7 mmoles) of 4-(3-trifluoromethylphenyl)-1,2,3,6-tetrahydropyridine are added thereto. The mixture is refluxed for 4 hours, the solvent is evaporated off and is washed with water. It is extracted with methylene chloride, the organic phase is dried and the solvent is evaporated off under reduced pressure. The residue is purified by silica gel column chromatography in eluting with a cyclohexane/ethyl acetate mixture=8/2. The hydrochloride is prepared with the aid of isopropanol saturated with HCl. The title compound is obtained. M.p. 244-245° C.

The invention claimed is:
1. A method of inhibiting apoptosis in a patient with prion disease which comprises administering an effective amount of a compound selected from 1-[2-(6,7-methylenedioxynaphth-2-yl)ethyl]-4-(3-trifluoromethylphenyl)-1,2,3,6-tetrahydropyridine, 1-[2-(4-cyclohexenylphenyl)-ethyl]-4-(3-trifluoromethylphenyl)-1,2,3,6-tetrahydropyridine and 1-[2-biphenyl-4-yl)ethyl]-4-(2-trifluoromethylphenyl)-1,2,3,6-tetrahydropyridine or a pharmaceutically acceptable salt thereof.

* * * * *